Figure 1:
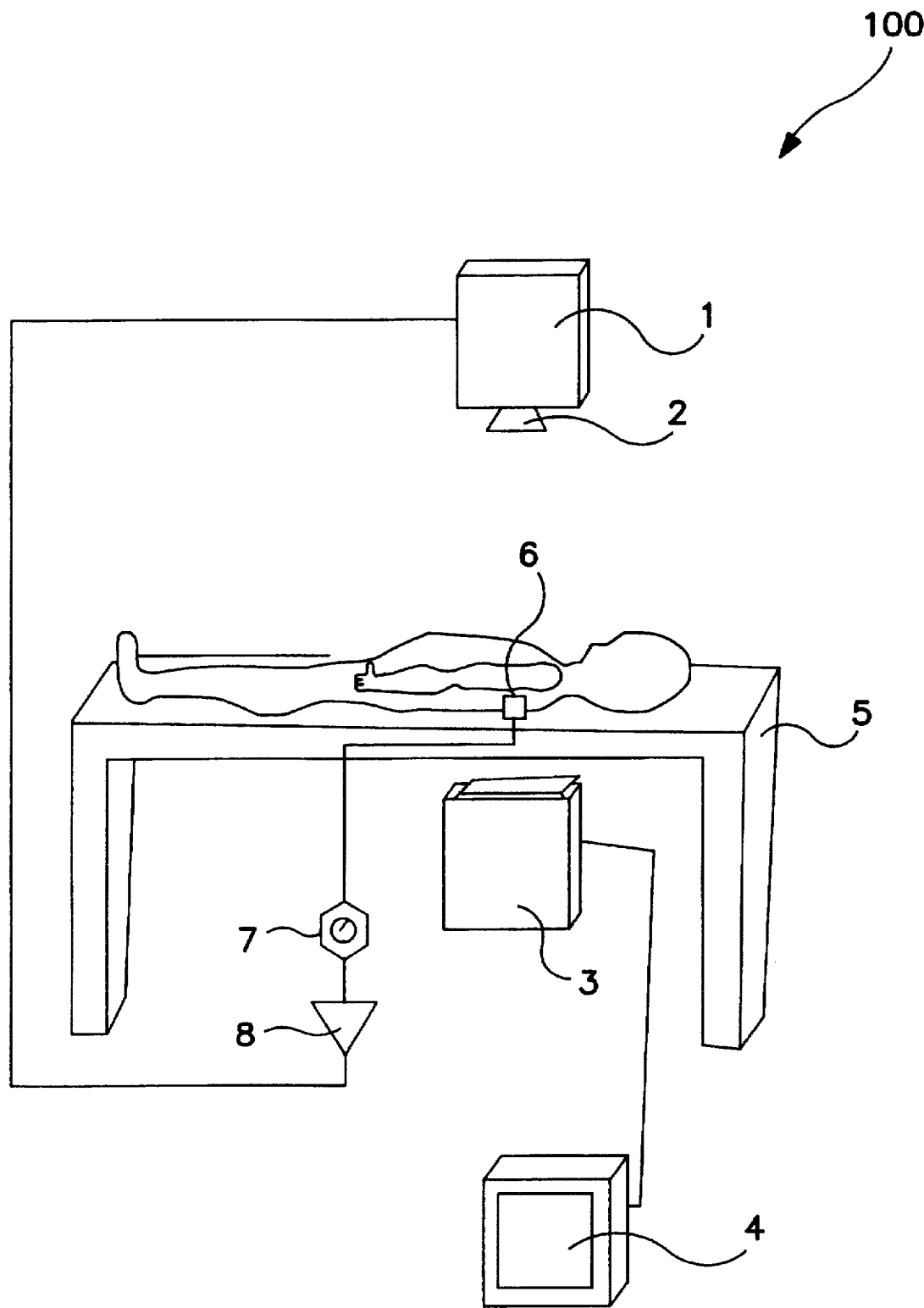

United States Patent [19]

Krause et al.

[11] Patent Number: 5,896,439
[45] Date of Patent: Apr. 20, 1999

[54] PROCESS FOR AVOIDING RADIATION INJURY IN DIAGNOSTIC RADIOLOGY

[75] Inventors: Werner Krause; Uwe Krüger, both of Berlin; Peter Muschik, Ladeburg, all of Germany

[73] Assignee: Schering Aktiengesellschaft, Germany

[21] Appl. No.: 08/737,528

[22] PCT Filed: May 12, 1995

[86] PCT No.: PCT/DE95/00649

§ 371 Date: Jul. 3, 1997

§ 102(e) Date: Jul. 3, 1997

[87] PCT Pub. No.: WO95/31134

PCT Pub. Date: Nov. 23, 1995

[30] Foreign Application Priority Data

May 13, 1994 [DE] Germany .................. 44 17 287

[51] Int. Cl.$^6$ ...................................... H61B 6/00
[52] U.S. Cl. .............................. 378/95; 378/98.2
[58] Field of Search .................. 378/95, 98.2, 98.12, 378/98, 98.11, 207, 8, 162, 163

[56] References Cited

U.S. PATENT DOCUMENTS

| | | | |
|---|---|---|---|
| 4,477,923 | 10/1984 | Baumann et al. | 378/95 |
| 4,611,340 | 9/1986 | Okazaki | 378/95 |
| 4,881,124 | 11/1989 | Yokouchi et al. | 378/98.12 X |
| 5,111,492 | 5/1992 | Klausz | 378/98.2 |

FOREIGN PATENT DOCUMENTS

| | | |
|---|---|---|
| 0 465 359 A1 | 1/1992 | European Pat. Off. . |
| 0 616 791 A2 | 9/1994 | European Pat. Off. . |
| 1 125 560 | 3/1962 | Germany . |
| 34 31 538 A1 | 3/1986 | Germany . |

OTHER PUBLICATIONS

Holik, Von B., Methode zur Vermeidung der Becken–Bein–Angiographie miy schrittweiser Tischplattenverschiebung, Electromedia, vol. 45, No. 1, pp. 2–6, 1977.

*Primary Examiner*—David P. Porta
*Attorney, Agent, or Firm*—Miller, White, Zelano, & Branigan, P.C.

[57] ABSTRACT

The invention relates to a process for avoiding radiation injury in diagnostic radiology by measuring the change in concentration of endogenous substances in bodily fluids. In addition, the invention comprises a device for implementing this process.

5 Claims, 1 Drawing Sheet

PROCESS FOR AVOIDING RADIATION INJURY IN DIAGNOSTIC RADIOLOGY

The invention relates to the object characterized in the claims, i.e., a process for avoiding radiation injury in diagnostic radiology, as well as a device for implementing this process.

In the case of some modern radiological problems, especially in contrast-enhanced computer tomography, the recording time is to be synchronized with the arrival of the contrast medium bolus in the tissue section in question. This is especially necessary in the case of vasography (CT angiography). At present, the exact transit time of the contrast medium bolus from the injection site to the particular tissue section can be only roughly estimated. Today, the problem that the arrival of the contrast medium bolus in the tissue to be examined can be determined only imprecisely is generally solved by triggering the x-ray source even before this contrast medium bolus arrives. The drawback to this approach consists in the fact that the irradiation lasts longer than absolutely necessary. A solution to this problem is described in German laid-open specification DE 42 18321 A1. The diagnostic system that is indicated there has the drawback that the measurement of the contrast medium bolus is done either by a radioisotope source, which in turn contributes to the radiation exposure of the patient or, on the other hand, by adding an optically detectable dye, which for its part increases the foreign substance burden on the patient.

Therefore, there is still a need for a process that allows synchronization with the contrast medium bolus at the x-ray source, without unnecessarily burdening the patient with foreign substances or additional radiation.

This object is achieved by the process according to the invention and the device for implementing this process.

The process according to the invention consists in the fact that the natural components of the blood stream or lymph tract are measured with the aid of a sensor. When the contrast medium bolus arrives at the tissue to be examined, the natural bodily fluid is displaced (diluted) by the arrival of the contrast medium. The change in the physical properties of the bodily fluids can be measured and produce the necessary signal for triggering the x-ray device. In an advantageous embodiment of the process according to the invention, the concentration of the blood pigment hemoglobin is measured by, for example, transmission or reflection spectroscopy. When the signal drops below an adjustable setpoint value, the x-ray source is triggered.

The process according to the invention has the advantage that the arrival time of the contrast medium bolus in a specific tissue section can be precisely determined without additional radiation or foreign substance burden. In another advantageous embodiment of this process, it is also possible to measure the drainage of contrast medium. As a result, it is possible to limit the irradiation time of the patient to the time during which a sufficient amount of contrast medium is available in the tissue that is to be examined.

Preferred is a process whereby the sensor is a measurement device for determining the concentration of blood components. Especially preferred is a process in which the concentration of hemoglobin is determined by transmission or reflection spectroscopy. For measurement, the light sensor of a device (e.g., Multiscan OS 10 or OS 15) is placed on the skin over a peripheral vein or artery. As a result, the absolute hemoglobin content of the blood can be determined. After a medium, e.g., a contrast medium that is commonly used in CT is injected, the hemoglobin concentration briefly dips, and a signal that can be picked up by a sensor is thus produced. This signal is processed by the setpoint switch. If the signal is adequate, the pulse generator activates the radiation source. After the contrast medium bolus passes through the examination area, the sensor detects the rise in hemoglobin concentration. After a setpoint is exceeded, the radiation source is shut off.

Another embodiment consists in the fact that the sensor is a flow gauge. Since the media frequently have a viscosity that is different from that of the blood, a change of flow rate occurs which can be found in this way. In addition, some media have an inductivity that is different from that of the blood, so that even if the medium and the bodily fluid have the same viscosity, the medium can be located more reliably. Further, it is also possible to measure the displacement of bodily fluids by sonography (with the aid of Doppler sonography).

The process according to the invention is carried out with the aid of the device that is described below and depicted in FIG. 1. Circuit (100) consists of a radiation source (1) with a radiation window (2). A detector (3), which displays an image on a monitor (4), is placed opposite the radiation window. A table (5) on which the patient lies is between the x-ray device and the detector. When the veins in the upper arm are visualized, it is sensible to place a sensor (6) on the patient's skin proximal to the diagnosis area. This sensor measures the hemoglobin concentration in the blood. The sensor is coupled to a setpoint switch (7), which records the change in hemoglobin concentration in the upper arm. If a threshold value is not exceeded, a pulse generator (8) is activated which turns on the x-ray source. When the hemoglobin concentration increases again, the latter is also recorded by sensor (6), which, after adjustment with setpoint switch (7), causes pulse generator (8) to turn off the x-ray source again.

In doing so, the patient is irradiated at the correct moment; additional pre-transit time and post-transit time are no longer necessary for the actual diagnosis.

Necessary sensor (6) is, for example, a measurement device for determining the flow rate or inductivity of bodily fluids. Preferably, the sensor is a transmission or reflection spectrometer. Further preferred is a sonographic sensor, especially a measuring head, that is suitable for Doppler sonography.

The invention therefore also relates to a device for implementing the process according to the invention.

We claim:

1. A process for avoiding radiation injury in diagnostic radiology, which comprises measuring the arrival of a contrast medium bolus in a specific tissue by detecting the displacement of an endogenous substance in a bodily fluid, whereby the detecting is carried out by transmission or reflection spectroscopy or by sonography.

2. Process according to claim 1, whereby the bodily fluid is blood or lymph.

3. Process according to claim 1, whereby the endogenous substance is hemoglobin.

4. A device for implementing a process for avoiding radiaton injury in diagnostic radiology, comprising
   - a radiation source (1),
   - a sensor (6), which measures a change in concentration of an endogenous substance in a bodily fluid by transmission or reflection spectroscopy or by ultrasound,
   - a setpoint switch (7), which compares the measured change in concentration with a setpoint, and
   - a pulse generator (8), which controls the turning on and off of the radiation source.

5. Circuit according to claim 4, whereby the sensor is a measurement device for determining hemoglobin.

\* \* \* \* \*